United States Patent [19]
Badoz

[11] Patent Number: 5,897,318
[45] Date of Patent: Apr. 27, 1999

[54] SLEEVE FOR A ROTARY DENTAL INSTRUMENT

[75] Inventor: Jean-Marie Badoz, Doubs, France

[73] Assignee: Micro-Mega International Manufactures, Besancon, France

[21] Appl. No.: 08/840,742

[22] Filed: Apr. 16, 1997

[30] Foreign Application Priority Data

Apr. 17, 1996 [FR] France ................................. 96 04988

[51] Int. Cl.⁶ ........................................................ A61C 3/02
[52] U.S. Cl. ........................................... 433/165; 408/226
[58] Field of Search .................................... 433/102, 134, 433/135, 165, 166; 408/226; 81/177.1

[56] References Cited

U.S. PATENT DOCUMENTS

| | | | |
|---|---|---|---|
| 628,927 | 7/1899 | Ducharme | 81/177.1 |
| 2,606,366 | 8/1952 | Stevens | 433/166 |
| 2,871,899 | 2/1959 | Coyle et al. | 81/177.1 |
| 4,321,040 | 3/1982 | Miller et al. | 433/102 |
| 4,451,237 | 5/1984 | Filhol | 433/165 |
| 4,478,578 | 10/1984 | Leonard | 433/165 |
| 4,802,848 | 2/1989 | Randin | 433/134 |

FOREIGN PATENT DOCUMENTS 1126560  3/1962  Germany ............................... 433/166

*Primary Examiner*—Ralph A. Lewis
*Attorney, Agent, or Firm*—Weiser and Associates, P.C.

[57] ABSTRACT

The sleeve has a cylindrical metal tube with a plastic core. The metal tube has one or more grooves on the inner surface of the tube that run along at least a portion of the length of the tube. The plastic core fills the annular space between the metal tube and the rod of a rotary dental instrument, such that plastic material (1) fills the grooves to anchor the plastic core to the metal sleeve and (2) is molded to rigidly link the rod to the sleeve. The present invention reduces the exposure of plastic material in the sleeve, thereby reducing plastic swelling that can occur when the dental instrument is repeatedly cleaned using disinfectants.

9 Claims, 1 Drawing Sheet

SLEEVE FOR A ROTARY DENTAL INSTRUMENT

BACKGROUND OF THE INVENTION

1. Field of the Invention

The present invention relates to dentistry equipment, and, in particular, to sleeves for rotary dental instruments, such as those for treating tooth cavities.

2. Description of the Related Art

Instruments used in dental surgery require absolute hygiene which obliges dentists to regularly clean and disinfect the instruments. This repeated cleaning and disinfecting can actually damage the sleeves that are often part of rotary dental instruments. In particular, aluminum sleeves may be attacked by the disinfectants, and plastic sleeves may swell under the effect of formaline, which is often used as a disinfectant.

To overcome these drawbacks, French patent 2 499 446 describes a mixed sleeve, namely one that is not solely made of plastic, which enables the sleeve to be less sensitive to cleaning or disinfecting. Nevertheless, the sleeve described in the patent has some drawbacks. In particular, the patent describes anchoring means in the form of a perforation or opening in a cylindrical metal tube where plastic material projects into that opening. Such anchoring means have the drawback that, when the user cleans and/or disinfects the instrument with products that cause plastic to swell, the plastic material in the sleeve will protrude slightly from the outer surface of the cylindrical metal tube and thereby form a projection that may make it difficult to place the instrument in the hand-piece.

Moreover, application of the invention of French patent 2 499 446 to certain types of dental instruments would require a redesign of how the cylindrical metal tube is manufactured which would cause the manufacturing process to be more expensive.

The present invention addresses the drawbacks of the devices of the prior art as described above. Aspects and advantages of this invention will become apparent from the detailed description which follows.

SUMMARY OF THE INVENTION

The present invention is directed to a sleeve for a dental instrument having a rod with a rotary inner channel. The sleeve comprises (a) a cylindrical metal tube having one or more grooves on the inner surface of the tube that run along at least a portion of the length of the tube, and (b) a plastic core having plastic material filling the one or more grooves in the tube to anchor the plastic core to the tube and adapted to firmly hold part of the rod of the dental instrument within the sleeve.

BRIEF DESCRIPTION OF THE DRAWINGS

Other aspects, features, and advantages of the present invention will become more fully apparent from the following detailed description, the appended claims, and the accompanying drawings in which:

DETAILED DESCRIPTION

The present invention is directed to sleeves for rotary dental instruments having a rod and an inner rotary channel. According to embodiments of the present invention, a sleeve has a cylindrical metal tube and a plastic core. The tube has one or more grooves that run along its inner surface for at least part of the length of the tube. The grooves may extend to one or both ends of the tube or fail to extend to either end, depending on the implementation. Plastic material of the core fills the grooves to form anchoring means that secure the plastic core to the metal tube. The plastic core is adapted to receive and firmly hold part of the rod of a rotary dental instrument within the sleeve. The plastic core fills the annular space between the metal tube and the instrument rod thereby forming a single integrated device. The rod extends beyond the sleeve to form the instrument head. Since the plastic core is held in place with respect to the metal tube within one or more grooves in the metal tube (rather than within a perforation in the metal tube), the sleeve of the present invention provides minimal exposure of plastic material. As such, there is less danger that the plastic material will swell when the dental instruments are repeatedly cleaned using disinfectants.

Figure 1:
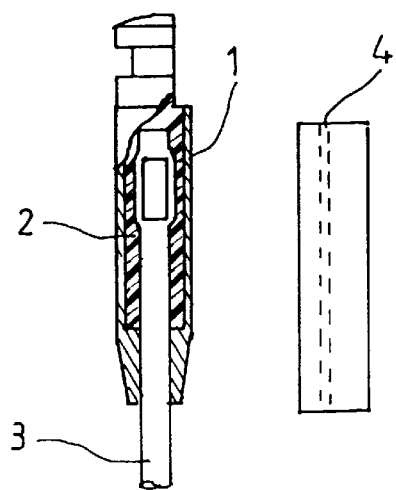
FIG. 1 shows a front view and a partial cross-sectional view of a sleeve, according to one embodiment of the present invention.

FIG. 1 shows a front view and a partial cross-sectional view of a sleeve for a rotary dental instrument, according to one embodiment of the present invention. The sleeve comprises a hollow cylindrical metal tube (1) with a plastic core (2) molded inside the metal tube. The tube may be made, for example, of copper-nickel-zinc alloy, nickel-plated brass, or stainless steel, which are more resistant to damage from disinfectants than is aluminum. The rod (3) of the rotary dental instrument is inserted during the molding of the sleeve (1) so that its central axis is approximately aligned with the central axis of the sleeve tube. The rod (3) is embedded in the plastic core (2) and thus rigidly linked to the core and the metal tube.

Figure 2:
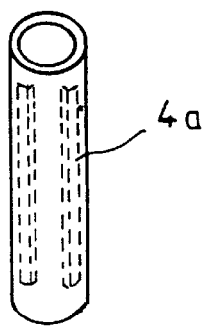
FIGS. 2–4 show perspective views of sleeve tubes corresponding to three different embodiments of the sleeve of FIG. 1.
Figure 3:
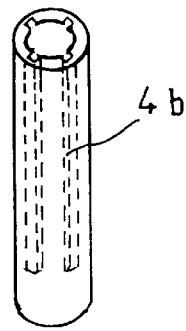
Figure 4:
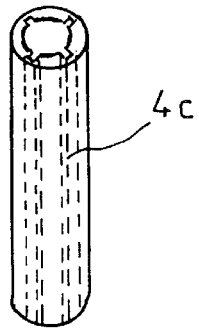

FIGS. 2–4 show perspective views of sleeve tubes corresponding to three different embodiments of the sleeve of FIG. 1. In FIG. 2, the grooves do not extend all the way to the ends of the metal tube. In FIG. 3, the grooves extend to only one end of the metal tube. In FIG. 4, the grooves extend to both ends of the metal tube.

Figure 5:
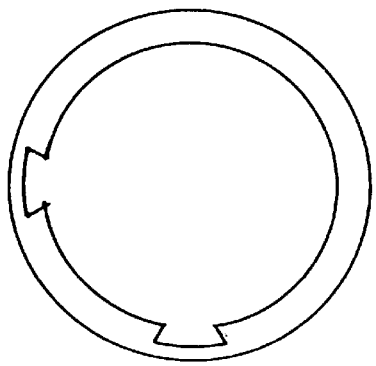
FIGS. 5–6 shows partial sectional views of sleeve tubes corresponding to two different embodiments of the sleeve of FIG. 1.
Figure 6:
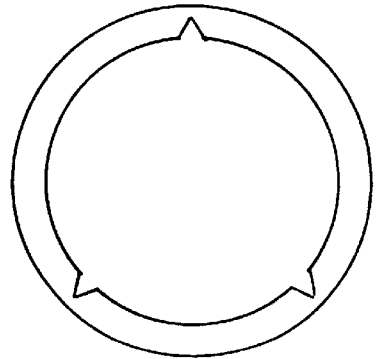

FIGS. 5–6 shows partial sectional views of sleeve tubes corresponding to two different embodiments of the sleeve of FIG. 1. In FIG. 5, the grooves have a dovetail shape. In FIG. 6, the grooves have a V shape.

Because less plastic material is exposed, the present invention provides sleeves that are less fragile and more resistant to swelling caused by disinfectants used in the repetitive cleaning of dental instruments.

It will be understood that various changes in the details, materials, and arrangements of the parts which have been described and illustrated in order to explain the nature of this invention may be made by those skilled in the art without departing from the principle and scope of the invention as expressed in the following claims.

What is claimed is:

1. A sleeve for positioning a rotatable rod within an inner channel of a dental instrument, the sleeve comprising:

(a) a cylindrical metal tube having one or more longitudinal grooves on the inner surface of the tube that ran along at least a portion of the length of the tube; and (b) a plastic core having plastic material filling the one or more longitudinal grooves in the tube to anchor the plastic core to the tube and adapted to firmly hold part of the rod of the dental instrument within the sleeve, wherein the one or more longitudinal grooves fail to extend to either end of the tube thereby inhibiting exposure of any of the plastic material to disinfectants during cleaning of the sleeve.

2. The sleeve of claim 1, wherein the one or more longitudinal grooves have either a dovetail shape or a V shape.

3. The sleeve of claim 1, wherein the tube is made of a metal that is resistant to damage from disinfectants.

4. The sleeve of claim 3, wherein the tube is made of either a copper-nickel-zinc alloy, nickel-plated brass, or stainless steel.

5. A dental instrument, comprising:

(a) a cylindrical metal tube, the tube having one or more longitudinal grooves on the inner surface of the tube that run along at least a position of the length of the tube;

(b) a rotatable rod located partially within the metal tube; and (c) a plastic core having plastic material filling the one or more longitudinal grooves in the tube and annular space between the rod and the metal tube, wherein the plastic core is anchored to the tube and the rod is rigidly linked to the plastic core and thereby to the metal tubes, wherein the one or more longitudinal grooves fail to extend to either end of the tube thereby inhibiting exposure of any of the plastic material to disinfectants during cleaning of the sleeve.

6. The dental instrument of claim 5, wherein the one or more longitudinal grooves have either a dovetail shape or a V shape.

7. The dental instrument of claim 5, wherein the tube is made of a metal that is resistant to damage from disinfectants.

8. The dental instrument of claim 7, wherein the tube is made of either a copper-nickel-zinc alloy, nickel-plated brass, or stainless steel.

9. A process for manufacturing a rotary dental instrument having a rotatable rod within an inner channel of the dental instrument, comprising the steps of:

(a) inserting the rod into a sleeve comprising a cylindrical metal tube with a plastic core, the tube having one or more longitudinal grooves on the inner surface of the tube that run along at least a portion of the length of the tubes, wherein the one or more longitudinal grooves fail to extend to either end of the tube thereby inhibiting exposure of any of the plastic material to disinfectants during cleaning of the sleeve; and (b) molding the plastic core such that plastic material (1) fills the one or more longitudinal grooves to anchor the plastic core to the metal tube and (2) rigidly links the rod to the sleeve.

* * * * *